(12) United States Patent
Newton et al.

(10) Patent No.: US 10,238,511 B1
(45) Date of Patent: Mar. 26, 2019

(54) ELECTROMAGNETIC SUSPENSION SYSTEM FOR PROSTHETIC DEVICE

(76) Inventors: Kaione R. Newton, Honolulu, HI (US); Timothy J. Roe, Honolulu, HI (US)

( * ) Notice: Subject to any disclaimer, the term of this patent is extended or adjusted under 35 U.S.C. 154(b) by 346 days.

(21) Appl. No.: 13/507,992

(22) Filed: Aug. 10, 2012

Related U.S. Application Data (60) Provisional application No. 61/574,956, filed on Aug. 12, 2011.

(51) Int. Cl.
*A61F 2/80* (2006.01)
*A61F 2/78* (2006.01)
*A61F 2/76* (2006.01)

(52) U.S. Cl.
CPC ............................ *A61F 2/80* (2013.01); *A61F 2/76* (2013.01); *A61F 2/78* (2013.01); *A61F 2/7812* (2013.01); *A61F 2002/7818* (2013.01)

(58) Field of Classification Search
CPC ........................................................ A61F 2/80
USPC .......................................................... 623/33
See application file for complete search history.

(56) References Cited

U.S. PATENT DOCUMENTS

| | | | |
|---|---|---|---|
| 4,024,588 A | 5/1977 | Janssen et al. | |
| 4,075,589 A | 2/1978 | Braillon | |
| 4,332,037 A | 6/1982 | Esformes et al. | |
| 4,743,264 A | 5/1988 | Sherva-Parker | |
| 4,781,720 A | 11/1988 | Sherva-Parker | |
| 5,507,835 A | 4/1996 | Jore | |
| 6,002,317 A | 12/1999 | Pignataro | |
| 6,063,125 A | 5/2000 | Arbogast et al. | |
| 6,229,422 B1 | 5/2001 | Pignataro | |
| 6,273,918 B1 | 8/2001 | Yuhasz et al. | |
| 6,387,096 B1 | 5/2002 | Hyde, Jr. | |
| 6,605,118 B2 | 8/2003 | Capper et al. | |
| 6,797,008 B1 | 9/2004 | Arbogast et al. | |
| 7,033,400 B2 | 4/2006 | Currier | |
| 7,144,429 B2 | 12/2006 | Carstens | |
| 7,291,182 B1 | 11/2007 | Kania | |
| 7,817,004 B2 | 10/2010 | Fullerton et al. | |
| 7,850,740 B2 | 12/2010 | Cox et al. | |
| 7,914,586 B2 | 3/2011 | Haines | |
| 7,922,773 B1 | 4/2011 | Kuiken | |
| 7,947,085 B2 | 5/2011 | Haines et al. | |
| 2004/0098136 A1 * | 5/2004 | Caspers | 623/34 |
| 2004/0143345 A1 | 7/2004 | Caspers | |
| 2006/0293762 A1 | 12/2006 | Schulman et al. | |
| 2007/0191965 A1 | 8/2007 | Colvin et al. | |
| 2008/0243266 A1 | 10/2008 | Haynes et al. | |

(Continued)

*Primary Examiner* — Jacqueline Woznicki (57) ABSTRACT

A suspension system and method for attaching a prosthetic device to a residual limb. In an illustrative embodiment, the suspension system comprises: a prosthetic socket that is attached to the prosthetic device; a socket adaptor that is incorporated into the prosthetic socket, the socket adaptor comprising a power supply, a microprocessor, and a power switch; a plurality of electromagnets, electropermanent magnets or electroadhesors that are arranged in an array and embedded in said prosthetic socket, each of said electromagnets, electropermanent magnets or electroadhesors being connected to the socket adaptor; a magnetically active liner that is adapted to be in intimate contact with said residual limb and that is fabricated from a magnetically active material; and a locking pin that protrudes from said magnetically active liner and that is adapted to attach the liner to the socket.

16 Claims, 4 Drawing Sheets

(56) References Cited

U.S. PATENT DOCUMENTS

2009/0254196 A1* 10/2009 Cox et al. .................. 623/33
2009/0292371 A1* 11/2009 Fullerton et al. ............ 623/57
2010/0289359 A1     11/2010 Knaian et al.

* cited by examiner

ELECTROMAGNETIC SUSPENSION SYSTEM FOR PROSTHETIC DEVICE

CROSS-REFERENCES TO RELATED APPLICATIONS

This application claims the benefit of U.S. Provisional Patent Application No. 61/574,956, filed Aug. 12, 2011, the disclosure of which patent application is incorporated by reference as if fully set forth herein.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

This invention relates to prosthetic devices. In particular, the invention relates to a suspension system and method for a prosthetic device.

The suspension system for a prosthetic device serves to attach the device to the user's body. Commonly, a prosthetic device is attached to the remains of an extremity (e.g., a residual limb). It is necessary for the suspension system to ensure a comfortable fit of the prosthesis. It must also allow for the prosthesis to be easily and accurately controlled by the user and must ensure that forces exerted on the prosthesis are properly transmitted to the user's body via the residual limb.

A common complication of prosthetic device use is a reduction in volume of the residual limb during use of the prosthesis. This is due in part to pressure from the prosthetic socket on the limb, compressing tissue. Other medical factors including the user's internal fluid volume status may also have an effect. Loss of residual limb volume can lead to loosening, improper distribution of weight bearing forces and poor fit of the limb in the socket. This can cause increases in pressure and shear force on the limb, potentially leading to skin breakdown. It also results in a reduction of control over the prosthesis.

The current state of the art in prosthetic fabrication calls for the custom fabrication of a rigid socket which can contain the residual limb. The residual limb is covered with a liner made of elastomeric gel, polymer foam, fabric or other material. The socket is designed to have intimate contact with the liner-clad limb. A goal of the suspension system is to allow for good control of the prosthesis, and to resist the effects of changes in limb volume.

Methods of prosthetic suspension have been developed to address the problems of prosthetic control and control of limb volume changes. Historically, fabrication techniques did not allow for precise fabrication of a socket providing intimate contact. Much of the suspension was provided by straps, suspension sleeves or the passive suction created by placing the limb into the socket. This resulted in a looser fitting socket which reduced prosthetic control. Limb volume changes were addressed with donning or doffing of additional liners to make up for changes in volume.

Improvements in prosthetic design and fabrication now allow for more precise fabrication of the socket providing for intimate fit. Suspension is achieved with the use of a silicone liner with a locking pin, a suction socket with passive vacuum, and/or the use of a vacuum pump to create a vacuum within the socket, referred to as Vacuum Assisted Suspension or (VAS).

The background art is characterized by U.S. Pat. Nos. 4,075,589; 4,743,264; 4,781,720; 5,507,835; 6,002,317; 6,063,125; 6,229,422; 6,273,918; 6,387,096; 6,605,118; 6,797,008; 7,033,400; 7,144,429; 7,291,182; 7,817,004; 7,850,740; 7,914,586; 7,922,773; and 7,947,085; and U.S. Patent Application Nos. 2004/0143345; 2006/0293762; 2007/0191965; 2008/0243266; and 2010/0289359; the disclosures of which patents and published patent applications are incorporated by reference as if fully set forth herein.

BRIEF SUMMARY OF THE INVENTION

As used herein, the following terms and variations thereof have the meanings given below, unless a different meaning is clearly intended by the context in which such term is used:

"A," "an," and "the" and similar referents used herein are to be construed to cover both the singular and the plural unless their usage in context indicates otherwise.

"About" means within 10 percent of a recited parameter or measurement, and preferably within 5 percent of such parameter or measurement.

"Comprise" and variations of the term, such as "comprising" and "comprises," are not intended to exclude other additives, components, integers or steps.

"Exemplary," "illustrative," and "preferred" mean "another."

One aspect of the invention is an electromagnet array incorporated into a prosthetic socket, with a magnetically active liner which provides both dynamic suspension and limb volume control for a prosthetic. Illustrative embodiments of the invention solve two major problems encountered by the prosthetic user. As a suspension system, an illustrative embodiment of the invention may be adjusted either manually or automatically to changes in prosthetic usage. This embodiment also serves to control limb volume to assure fit and prosthetic control and is consistent with current practice in prosthetic fabrication, allowing it to be readily adopted.

Illustrative embodiments of the invention do not require a tight seal between limb and socket, or the use of a heavy suspension sleeve in order to maintain vacuum suspension. These embodiments also comprise few moving parts that are likely to be damaged by the repetitive forces of ambulation.

By utilizing a magnetically active liner, the suspension system disclosed herein does not require surgical implantation. The liner is in intimate contact with the limb consistent with current prosthetic practice. A magnetically active external layer of the liner then interacts with the electromagnet array in the socket to achieve suspension and limb volume control.

The suspension system disclosed herein allows for placement of sensors within the socket or liner or in both of them, and for use of pressure and shear sensors in addition to load or position sensors. In addition, power to sensors and transmission of sensor signals to a central microprocessor is accomplished through electrical leads routed through the hub of the electromagnet array or through a conduit in the locking pin or lanyard.

In an illustrative embodiment, the suspension system disclosed herein utilizes a plurality of small electromagnets arranged in an array. This arrangement allows for uniform distribution of a magnetic field across the entire residual limb. It also allows for more precise control of the magnetic field in response to user adjustment or feedback from pressure sensors.

An illustrative embodiment of the invention is a suspension system for attaching a prosthetic device to a residual limb, said suspension system comprising: a prosthetic socket that is attached to the prosthetic device; a socket adaptor that is incorporated into said prosthetic socket, said socket adaptor comprising a power supply, a microprocessor, and a power switch and having a locking pin receptacle; a plurality of electromagnets, electropermanent magnets or electroadhesors that are arranged in a three-dimensional array and embedded in said prosthetic socket, each of said electromagnets being connected to said socket adaptor by a lead; a magnetically active liner that is comprised of an outer layer that is fabricated from a magnetically active material which may include electromagnets, electropermanent magnets, or electroadhesors and an inner layer that is composed of an elastomeric gel, said magnetically active liner being adapted to be in intimate contact with said residual limb; and a locking pin that protrudes from said magnetically active liner and that is adapted to fit into said locking pin receptacle and to attach the prosthetic device to the residual limb. In another embodiment, said electromagnets, electropermanent magnets or electroadhesors are attached to a support lattice. In another embodiment, said prosthetic socket is attached to the prosthetic device with a prosthesis connector. In another embodiment, the suspension system further comprises: one or more pressure sensors that are disposed in said prosthetic socket or in said magnetically active liner or in both of them and that are in electrical communication with said socket adaptor; one or more load sensors that are disposed in said prosthetic socket or in said magnetically active liner or in both of them and that are in electrical communication with said socket adaptor; one or more position sensors that are disposed in said prosthetic socket or in said magnetically active liner or in both of them and that are in electrical communication with said socket adaptor. In another embodiment, the suspension system further comprises: passive or active means for generating a suction (negative pressure) for attaching the magnetically active liner to the residual limb. In another embodiment, the suspension system further comprises: wired or wireless communication means for communication with said socket adaptor.

In another illustrative embodiment, the invention is a suspension system for attaching a prosthetic device to a residual limb, said suspension system comprising: a prosthetic socket that is attachable to the prosthetic device; a socket adaptor that is incorporated into said prosthetic socket, said socket adaptor comprising a power supply, a microprocessor, and a power switch and having a locking pin receptacle; a three-dimensional electromagnetic array that is embedded in the sidewalls of said prosthetic socket; and a magnetically active liner that is comprised of an outer layer and an inner layer, said magnetically active liner being operative to be in intimate contact with said residual limb.

In an illustrative embodiment, the electromagnetic array comprises a plurality of electromagnets or permanent magnets or electropermanent magnets or electroadhesors or a combination of them arranged in a three-dimensional array. The electromagnets may be air core or solid core coils based on field strength needs. They may be arranged in a "spider web" or grid fashion to facilitate fitting the three-dimensional array into the prosthetic socket. In this embodiment, the electromagnetic array is flexible to allow it to conform to the various shapes, typically cylindrical or conical, of different prosthetic sockets.

In an illustrative embodiment, the prosthetic socket is made using standard prosthetic fabrication materials and techniques. The electromagnet array is preferably incorporated into the body of the socket.

In an illustrative embodiment, the magnetically active liner comprises an inner layer that is composed of a silicone gel or a similar elastomeric gel and an outer layer. In this embodiment, the outer layer is comprised of a magnetically active material which is bonded to the liner. This magnetically active material may be a magnetic compound, a magnetically active material such as a ferromagnetic compound, a plurality of electromagnets, or a plurality of permanent magnets, electropermanent magnets, or electroadhesors, or a combination thereof. The magnetically active material may be incorporated into the outside layer in the form of plates, pellets, particles, fibers, films, or woven or braided fabric materials.

In an illustrative embodiment, a locking pin is incorporated into the liner. In this embodiment, the purpose of the locking pin is to provide a redundant suspension system in the event of power failure or other failure of the primary suspension system. The locking pin may also serve as a conduit for electrical leads from the socket adapter to the liner to allow for electromagnets, pressure sensors, or other devices to be incorporated into the liner. The locking pin may also serve as a conduit for transmission of suction (negative pressure) from a vacuum assist device in the socket adapter to the space between the liner and residual limb.

In an illustrative embodiment, the socket adapter serves as a processor and power supply for the electromagnet array. In this embodiment, the socket adapter is incorporated into the prosthetic socket and is connected to the electromagnet array. Contained within the adapter are the power supply and the electronic components for control of the suspension system. A microprocessor for control of the array and processing of sensor input may also be included. A power switch and battery power supply indicator are incorporated into the socket adapter, and additional manual controls may also be included. A wired and/or wireless communication device may also be included in the socket adapter to allow for adjustments to the electromagnet array to be made using a computer or a handheld device. The socket adapter also provides a locking receptacle for the locking pin, and incorporates a prosthesis connector for attachment to the distal prosthetic device.

In a further illustrative embodiment, the invention is a suspension system for attaching a prosthetic device to a residual limb, said suspension system comprising: a prosthetic socket that is attachable to the prosthetic device; a socket adaptor that is incorporated into said prosthetic socket, said socket adaptor comprising a power supply, a microprocessor, and a power switch and having a locking pin receptacle; a plurality of electropermanent magnets that are arranged in a three-dimensional array and embedded in the sidewalls of said prosthetic socket, each of said electropermanent magnets being connected to said socket adaptor by a lead; a magnetically active liner that is comprised of an outer layer that is fabricated from a magnetically active material and an inner layer that is composed of an elastomeric gel, said magnetically active liner being operative to be in intimate contact with said residual limb; and a locking pin that protrudes from said magnetically active liner and that is adapted to fit into said locking pin receptacle and to attach the prosthetic device to the residual limb. In another embodiment, said electropermanent magnets are attached to a support lattice. In another embodiment, said prosthetic socket is attached to the prosthetic device with a prosthesis connector. In another embodiment, the suspension system further comprises: one or more pressure sensors that are disposed in said prosthetic socket or in said magnetically active liner or in both of them and that are in electrical communication with said socket adaptor; one or more load sensors that are disposed in said prosthetic socket or in said magnetically active liner or in both of them and that are in electrical communication with said socket adaptor; and one or more position sensors that are disposed in said prosthetic socket or in said magnetically active liner or in both of them and that are in electrical communication with said socket adaptor. In another embodiment, the suspension system further comprises: active or inactive means for generating a suction for attaching said magnetically active liner to the residual limb. In another embodiment, the suspension system further comprises: wired or wireless communication means for communication with said socket adaptor.

In yet another illustrative embodiment, the invention is a suspension system for attaching a prosthetic device to a residual limb, said suspension system comprising: a prosthetic socket that is attachable to the prosthetic device; a socket adaptor that is incorporated into said prosthetic socket, said socket adaptor comprising a power supply, a microprocessor, and a power switch and having a locking pin receptacle; a plurality of electroadhesors that are arranged in a three-dimensional array and embedded in the sidewalls of said prosthetic socket, each of said electroadhesors being connected to said socket adaptor by a lead; a magnetically active liner that is comprised of an outer layer that is fabricated from a magnetically active material and an inner layer that is composed of an elastomeric gel, said magnetically active liner being operative to be in intimate contact with said residual limb; and a locking pin that protrudes from said magnetically active liner and that is adapted to fit into said locking pin receptacle and to attach the prosthetic device to the residual limb. In another embodiment, said electroadhesors are attached to a support lattice. In another embodiment, said prosthetic socket is attached to the prosthetic device with a prosthesis connector. In another embodiment, the suspension system further comprises: one or more pressure sensors that are disposed in said prosthetic socket or in said magnetically active liner or in both of them and that are in electrical communication with said socket adaptor; one or more load sensors that are disposed in said prosthetic socket or in said magnetically active liner or in both of them and that are in electrical communication with said socket adaptor; and one or more position sensors that are disposed in said prosthetic socket or in said magnetically active liner or in both of them and that are in electrical communication with said socket adaptor. In another embodiment, the suspension system further comprises: active or passive means for generating a suction for attaching said magnetically active liner to the residual limb. In another embodiment, the suspension system further comprises: wired or wireless communication means for communication with said socket adaptor.

In another illustrative embodiment, the invention is a suspension system for attaching a prosthetic device to a residual limb, said suspension system comprising: a liner comprising a material or objects to which a magnet is attracted, said liner being configured to conform with the outer surface of the residual limb; a prosthetic socket comprising a hollow body having sidewalls and an interior surface that is configured to conform with the shape of said liner when said liner is installed on the residual limb; a plurality of means for generating a magnetic field (e.g., electromagnets, electropermanent magnets, or electroadhesors) that are embedded in said sidewalls in a three-dimensional array, each of said electromagnets, electropermanent magnets, or electroadhesors having a magnetic moment with a direction that is substantially perpendicular to an adjacent portion of said interior surface; and a socket adapter with which said electromagnets, electropermanent magnets, or electroadhesors are in electrical communication, said socket adapter comprising a power supply, a microprocessor, and a power switch and being attachable to the prosthetic device. In another embodiment, the suspension system further comprises: a locking pin that protrudes from said liner and that is adapted to fit into a locking pin receptacle in said socket adapter to provide a redundent means of attachment the prosthetic device to the residual limb.

In a further illustrative embodiment, the invention is a suspension system for attaching a prosthetic device to a residual limb, said suspension system comprising: a liner comprising a material or objects to which a magnet is attracted, said liner being configured to conform with the outer surface of the residual limb; a prosthetic socket comprising a hollow body having sidewalls and an interior surface that is configured to conform with the shape of said liner when said liner is installed on the residual limb; a plurality of means for generating a magnetic field that are embedded in said sidewalls in a three-dimensional array, each of said means for generating a magnetic field having a magnetic moment with a direction that is substantially perpendicular to an adjacent portion of said interior surface; and a socket adapter with which said means for generating a magnetic field are in electrical communication, said socket adapter comprising a power supply, a microprocessor, and a power switch and being attachable to the prosthetic device.

Further aspects of the invention will become apparent from consideration of the drawings and the ensuing description of exemplary embodiments of the invention. A person skilled in the art will realize that other embodiments of the invention are possible and that the details of the invention can be modified in a number of respects, all without departing from the concept. Thus, the following drawings and description are to be regarded as illustrative in nature and not restrictive.

BRIEF DESCRIPTION OF THE SEVERAL VIEWS OF THE DRAWINGS

The features of the invention will be better understood by reference to the accompanying drawings which illustrate exemplary embodiments of the invention. In the drawings.

The following reference numerals are used to indicate the parts and environment of an illustrative embodiment of the invention on the drawings:

100 electromagnetic suspension system, system
101 residual limb
102 electromagnet array, array
103 liner
104 array arms, arms
105 prosthetic socket
106 sidewalls
107 electromagnet
108 permanent magnet
109 electrical lead
110 rare earth magnet
111 locking pin
112 foramen
113 array hub
114 socket adapter
115 support lattice
117 adaptor connector
119 locking pin receptacle, receptacle
121 manual locking pin release
123 power switch/array control
125 battery port
127 battery power indicator
129 prosthesis connector
131 liner electromagnet
133 liner sensors
135 adapter connector ring
137 prosthetic socket sensors
141 power supply
143 microprocessor, processor
145 power on/off switch
147 dial, button
151 magnetically active external layer, external layer
153 inner layer
155 vacuum assist device
157 body
160 wired or wireless communication device
161 computer or a handheld device
162 electropermanent magnet
164 electroadhesor
603 electrodes
605 dielectric material, dielectric
607 object of attraction
700 electrostatic latch
701 socket side electroadhesor
703 socket side dielectric layer
705 liner side electroadhesor
707 liner side dielectric

DETAILED DESCRIPTION OF THE INVENTION

Figure 1:
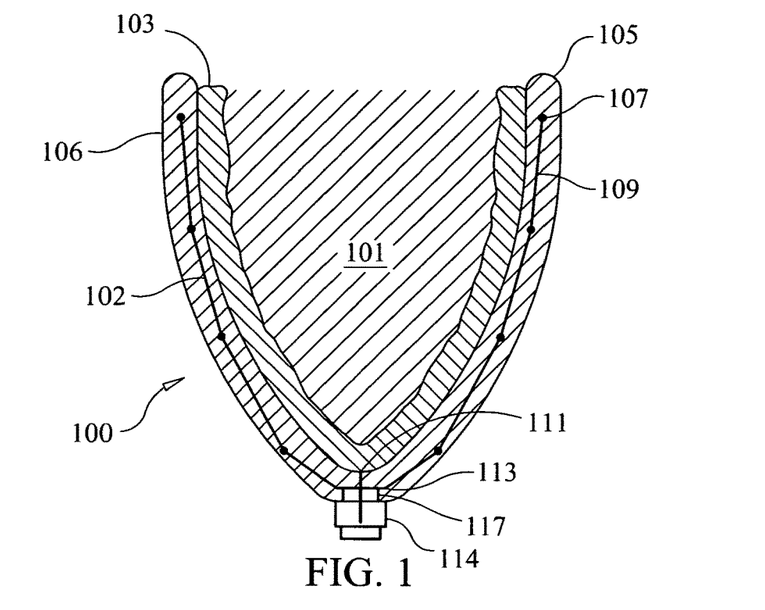
FIG. 1 is a cross sectional view of an illustrative embodiment of the invention installed on a residual limb.
Figure 4:
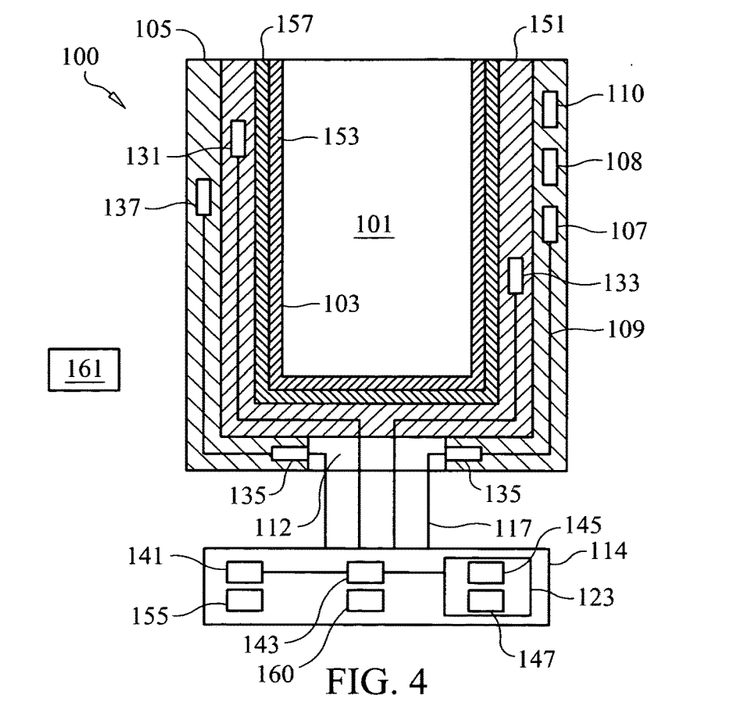
FIG. 4 is a cross sectional view of another illustrative embodiment of the invention.

Referring to FIGS. 1 and 4, two illustrative embodiments of electromagnetic suspension system 100 are shown. In the view shown in FIG. 1, electromagnetic suspension system 100 is installed on residual limb 101. Residual limb 101 is placed within and is in intimate contact with liner 103, which, in this embodiment, is magnetically active. The liner clad residual limb 101 is then placed within prosthetic socket 105 that comprises three-dimensional electromagnet array 102.

In a preferred embodiment, electromagnet array 102 comprises a plurality of electromagnets 107 that are connected with electrical leads 109. Preferably, array 102 comprises about 10 to about 100 electromagnets and most preferably comprises about 32 electromagnets that are imbedded in sidewalls 106 of prosthetic socket 105 and, in some embodiments, in liner 103. Electrical leads 109 terminate in array hub 113 which is situated in (preferably contained within) adapter connector ring 135 which is preferably disposed at the base of prosthetic socket 105. Electromagnetic array 102 may also comprise permanent magnets 108. In another embodiment, a plurality of electromagnets, electropermanent magnets, or electroadhesors are embedded in sidewalls 106 in a three-dimensional array, each of the electromagnets, electropermanent magnets, or electroadhesors having a magnetic moment with a direction that is substantially perpendicular to an adjacent portion of said interior surface.

Locking pin 111 is connected to and protrudes from liner 103, preferably extending through foramen (opening) 112 in the base of prosthetic socket 105 consistent with current prosthetic practice. Locking pin 111 may comprise additional electrical connections to liner electromagnets 131 or liner sensors 133 contained within liner 103, which, in this embodiment, is magnetically active. Locking pin 111 may also serve as a conduit for transmission of suction (negative pressure) from the vacuum assist device 155 to the interior of the liner 103.

Socket adapter 114 is preferably incorporated into the base of prosthetic socket 105. Locking pin 111 is inserted into socket adapter 114 through locking pin receptacle 119. Adapter connectors 117, containing electrical connections, extend from socket adapter 114 and connect to array hub 113 at adapter connector ring 135.

Figure 2:
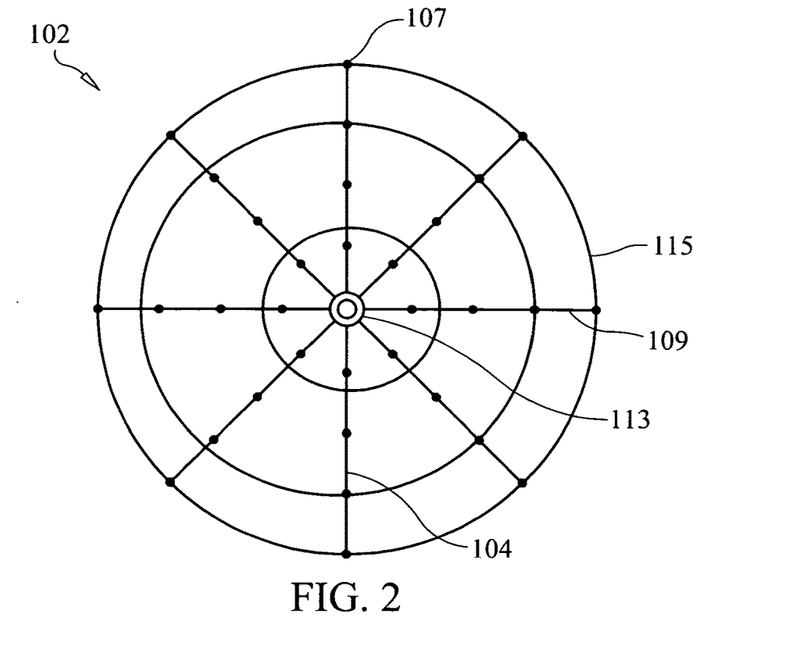
FIG. 2 is a (top) plan view of an electromagnet array in accordance with an illustrative embodiment of the invention.

Referring to FIGS. 2 and 4, two of many possible configurations for electromagnet array 102 are illustrated. In this view, a three-dimensional "spider web" configuration is shown, however, other configurations are possible including different numbers of electromagnets 107, different lengths of array arms 104, and different three-dimensional array shapes as needed to facilitate prosthetic fabrication. In the embodiment, illustrated in FIG. 2, thirty-two electromagnets 107 are connected to their electrical leads 109, which terminate in array hub 113 which is contained within the adapter connector ring 135. Three-dimensional support lattice 115 is shown which may comprise a material to support array 102 and facilitate prosthetic fabrication, and may contain additional electrical leads 109 for the array 102 or other electrical components such as prosthetic socket sensors 137. In some embodiments, a similar three-dimensional array is also present in liner 103. In other embodiments, liner 103 is fabricated from a magnetically active material to which a magnet is attracted.

Figure 3A:
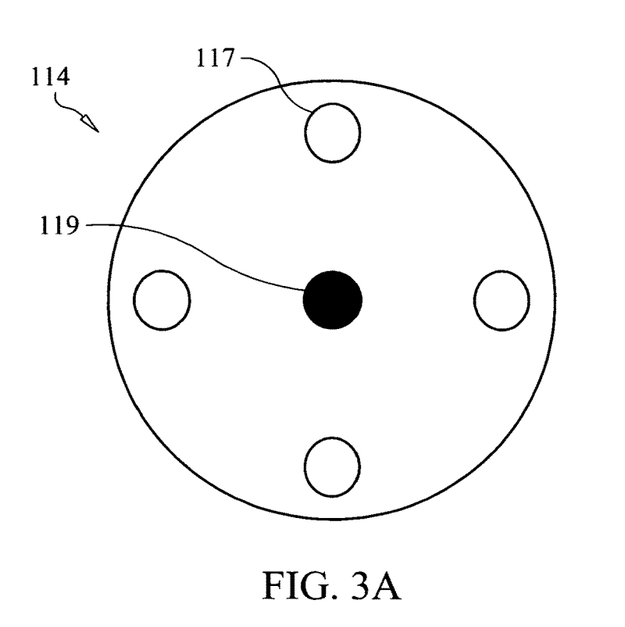
FIG. 3A is a (top) plan view of a socket adapter in accordance with an illustrative embodiment of the invention.
Figure 3B:
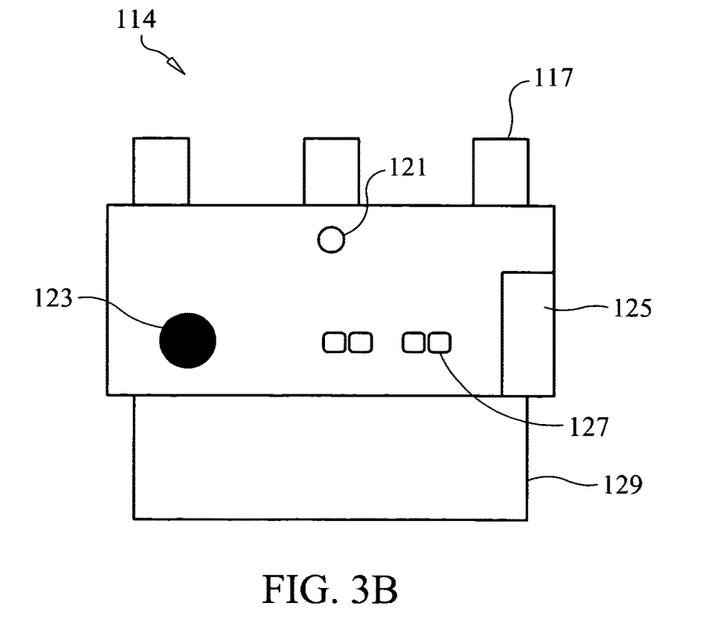
FIG. 3B is an elevation view of a socket adapter in accordance with an illustrative embodiment of the invention.

Referring to FIGS. 3A, 3B, and 4, two possible configurations of socket adapter 114 are illustrated. In these embodiments, socket adapter 114 comprises power supply 141, microprocessor(s) 143, and other electrical controls (e.g., power switch/array control 123 and battery power indicator 127) for electromagnet array 102. Socket adapter 114 also preferably comprises a prosthesis connector 129 for securing the distal end of the prosthesis to socket adapter 114. Socket adapter 114 is preferably incorporated into prosthetic socket 105 during fabrication of the prosthesis.

In this embodiment, socket adapter 114 features a plurality of adapter connectors 117, which contain electrical links and extend through the exterior wall of prosthetic socket 105 and connect to adapter connector ring 135. Locking pin receptacle 119 is preferably a mechanical, electromechanical, or electrical lock which secures locking pin 111 on insertion of locking pin 111 into receptacle 119. In this embodiment, manual locking pin release 121 is used to release locking pin 111 in the event of electrical failure of system 100.

Referring again to FIGS. 3A, 3B, and 4, other illustrative embodiments of system 1 are presented. In these embodiments, power switch/array control 123 provides manual control for system 100. Power switch/array control 123 may contain a power on/off switch 145 and may feature a dial or button 147 to allow the user to manually adjust the force of the electromagnetic field generated by array 102. Prosthesis connector 129 allows for the connection of a distal prosthetic component such as a pylon (not shown) to socket adapter 114.

In an illustrative embodiment, electromagnetic array 102 is incorporated into prosthetic socket 105 during fabrication using standard prosthetic fabrication techniques. The user is fitted with liner 103, which, in this embodiment, is magnetically active, also using standard prosthetic fabrication techniques. In use, the user dons liner 103 and then inserts his/her limb into prosthetic socket 105. In this embodiment, system 100 activates on engaging locking pin 11 into locking pin receptacle 119. System 100 may be alternately engaged and disengaged using power switch/array control 123.

When system 100 is engaged, power is supplied by power supply 141 in socket adapter 114 to electromagnet array 102. The magnetic field generated by array 102 attracts magnetically active external layer 151 of liner 103. The magnetic field force is preferably sufficient to ensure total contact of liner 103 with prosthetic socket 105.

The negative pressure created between liner 103 and residual limb 101 by an active means for generating suction (e.g., vacuum assist device 155) ensures total contact of residual limb 101 with liner 103. This creates an intimate fit between limb 101, liner 103 and prosthetic socket 105, promoting excellent control of the prosthetic device along with resisting limb volume changes. Vacuum assist devices for securing a residual limb in a prosthetic socket are known in the art. One such device is disclosed in U.S. Pat. No. 7,914,586; the disclosure of which patent is incorporated by reference as if fully set forth herein. A device similar to that disclosed in U.S. Pat. No. 7,914,586 is incorporated into an embodiment of socket adapter 114 to create a negative pressure between residual limb 101 and liner 103.

In an illustrative embodiment, liner sensors 133 incorporated into liner 103 or prosthetic socket sensors 137 incorporated into prosthetic socket 105 sense shear, pressure and limb volume within prosthetic socket 105. In this embodiment, sensor readings are processed by microprocessor 143 and adjustments are made to the field force of electromagnetic array 102 to redistribute pressure and adapt to changes in use of the prosthesis. To disengage system 100, the user turns off the power with power switch 123. In the event of a power failure, redundant suspension is provided by locking pin 111.

The composition of electromagnetic array 102 may include various different sizes of electromagnets 107 based on expected field strength needs. Electromagnet array 102 may comprise permanent magnets 108, electromagnets 107, or a combination of permanent magnets 108 and electromagnets 107. Rare earth magnets 110 may also be incorporated into electromagnet array 102.

Electromagnets 107 in array 102 may wired in individual circuits, wired in serial or parallel circuits, or a combination of individual, serial and parallel circuits. The number of electromagnets 107 in each arm 104 of array 102 may vary based on the application. Array 102 may be installed on the exterior surface or the interior surface of prosthetic socket 105 along with or instead of its being incorporated (imbedded) into prosthetic socket 105. Arms 104 of array 102 may have different lengths, and the number of arms 104 of array 102 may vary based on the application. Array 102 may be arranged in alternate shapes such as a circular grid, a square grid, or rectangular grid. Array 102 may be formed into a three dimensional shape such as a cup, cone, cylinder, cube, or sphere and may incorporate a (e.g., fabric) support lattice 115, which may contain electrical components.

Magnetically active embodiments of liner 103 may be made of any material that is attracted by a magnet, e.g., ferromagnetic materials or another magnet. In another embodiment, a magnetically active external layer 151 of liner 103 comprises magnetized compounds, electromagnets, or non-magnetized magnetically active compounds. In this embodiment, the magnetically active compounds in liner 103 may take various forms, including plates, discs, pellets, particles, fibers, strands, film, or woven or braided material. The magnetically active components of liner 103 may be situated in external layer 151, inner layer 153, or incorporated into body 157 of liner 103.

Multiple locking pins, a lanyard, or multiple lanyards may be used to provide a means for redundant (or backup) suspension. Locking pin 111 may also be used as a conduit for electronic communication with devices within or outside prosthetic socket 105. Locking pin 111 may also serve as a conduit for transmission of suction (negative pressure) from a vacuum assist device 155 in the socket adapter 114 to the space between liner 103 and residual limb 101. Sensors on the prosthetic device (not shown) may be incorporated into control of electromagnet array 102.

Socket adapter 114 may contain one or more microprocessors 143. Socket adapter 114 may contain wired or wireless communication means (e.g., wired or wireless communication device 160) using standards such as 3GPP LTE, IEEE 802.11, IEEE 1394, Bluetooth, CDMA, Universal Serial Bus, Firewire, Ethernet, Wi-Fi, or another method of electronic communication. The electronic control apparatus for magnetic array 102 may be capable of being adjusted by use of a computer or a handheld device 161.

Prosthetic socket 105 or liner 103 or both of them may contain shielding material to reduce electromagnetic emissions from system 100. Electromagnet suspension system 100 may be used to attach or stabilize an orthotic device. Liner 103 may require use of a lotion or ointment to promote an intimate fit with residual limb 101, maintain a negative pressure between liner 103 and residual limb 101, and aid in donning and doffing of liner 103. System 100 may also be used to provide an intimate fit between an intact limb and an adaptive device or tool, glove, gauntlet, shoe, or boot.

Figure 5:
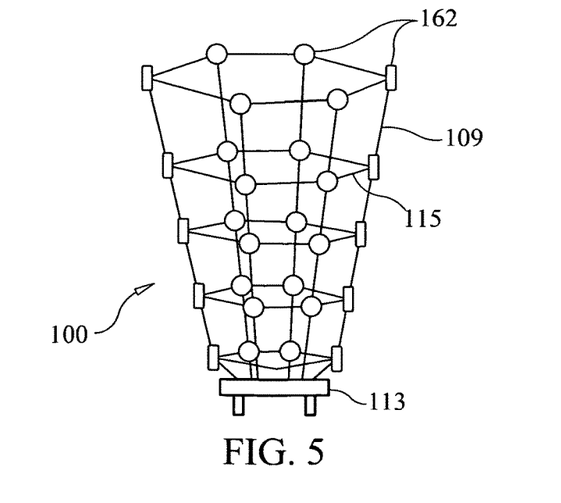
FIG. 5 is a perspective view of an electropermanent magnet array in accordance with an illustrative embodiment of the invention.

Referring to FIG. 5, a preferred embodiment of electromagnetic array 102 is presented. In this embodiment, prosthetic suspension force is provided by a microprocessor-controlled array 102 interacting with liner 103, which, in this embodiment, is magnetically active. Suspension force is dynamically adjusted based on feedback from sensors 133, 137 in liner 103 or in prosthetic socket 105 or in both of them.

In this embodiment, electropermanent magnets 162 are incorporated into liner 103 or in prosthetic socket 105 or in both of them. Electropermanent magnets 162 are magnetic assemblies whose holding force can be substantially modified by electrical pulses. An electropermanent magnet is a device which undergoes a substantial change in its magnetization upon stimulus with a current pulse. After the current is returned to zero or a low level, the magnetization remains substantially changed. An electropermanent magnet can receive energy in a short current pulse, and after the pulse is completed, continue to apply a magnetic force on another member through an air gap for a much longer time than the length of the pulse. Electropermanent magnets 162 are described in, for example, U.S. Pat. Nos. 4,075,589, 6,002,317, and 6,229,422; the disclosures of which patents are incorporated by reference as if fully set forth herein.

Initially developed for use in "ferreed" switches in telephone switching equipment, electropermanent magnets 162 are commonly used in large-scale magnetic cranes and in magnet grippers and chucks. An electropermanent magnet 162 is a solid-state device whose external magnetic field can be modulated by an electrical pulse. No electrical power is required to maintain the field, only to do mechanical work or to change the device's state. One example of an electropermanent magnet contains two magnetic materials, one magnetically hard (e.g., NdFeB) and one semi-hard, (e.g., Alnico), capped at both ends with a magnetically soft material (e.g., iron) and wrapped with a coil. A current pulse of one polarity magnetizes the materials together, increasing the external flow of magnetic flux. A current pulse of the opposite polarity reverses the magnetization of the semi-hard material, while leaving the hard material unchanged. This diverts some or all of the flux to circulate inside electropermanent magnet 162, reducing the external magnetic flux. The result is a programmable magnetic field strength with zero static power consumption.

A principal benefit of the use of electropermanent magnets 162 is that the strength of the magnetic force may be adjusted using current pulses. Pulsed current serves to significantly reduce the power demands of array 102 while also reducing the heat generated by array 102, particularly in comparison with the power demands and heat generation associated with traditional electromagnets 107. While in use, the flux produced by the electropermanent magnets 162 may be adjusted dynamically by microprocessor 143 in response to user demand or sensor data. Reversal of current polarity can then neutralize the magnetic force of array 102 to allow for easy doffing of the prosthetic device. Electropermanent magnets 167 may be used exclusively in array 102, or in combination with electromagnets 107 or permanent magnets 108. Electropermanent magnets 162 may be incorporated into prosthetic socket 105 or liner 103 or into both of them.

In another illustrative embodiment, system 100 comprises incorporating electrostatic adhesors into prosthetic socket 105 or liner 103 or into both of them. Electrostatic adhesion between two substances or surfaces occurs due to the presence of opposite charges, which attract each other. Electrostatic adhesion has been used industrially particularly in the paint and printing industries. In the early 1970s, it found application in the semiconductor industry in the form of an electrostatic wafer chuck used in semiconductor fabrication. In subsequent decades, there has been significant development in the use of electrostatic adhesion in material handling in the semiconductor industry and more recently in the field of robotics.

Figure 6A:
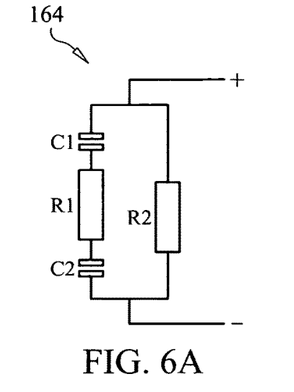
FIGS. 6A and 6B are schematic representations of an electroadhesor in accordance with an illustrative embodiment of the invention.
Figure 6B:
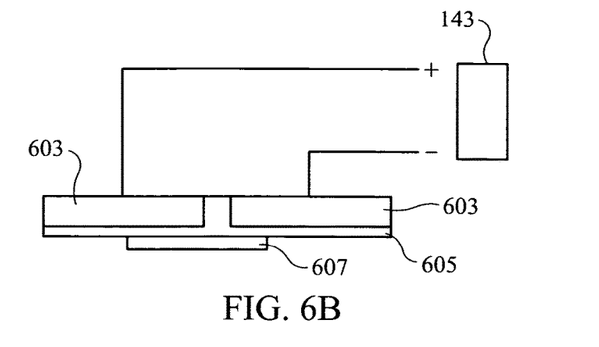

Referring to FIGS. 6A and 6B, a simplified schematic diagram of electroadhesor 164 is presented. In this embodiment, electrodes 603 are separated by dielectric material 605. Dielectric 605, for example a silicone polymer, allows for the passage and holding of the electrical charges generated at electrodes 603. The electrostatic charges then interact electrically with the surface of object of attraction 607 creating adhesion to dielectric 605.

Figure 7:
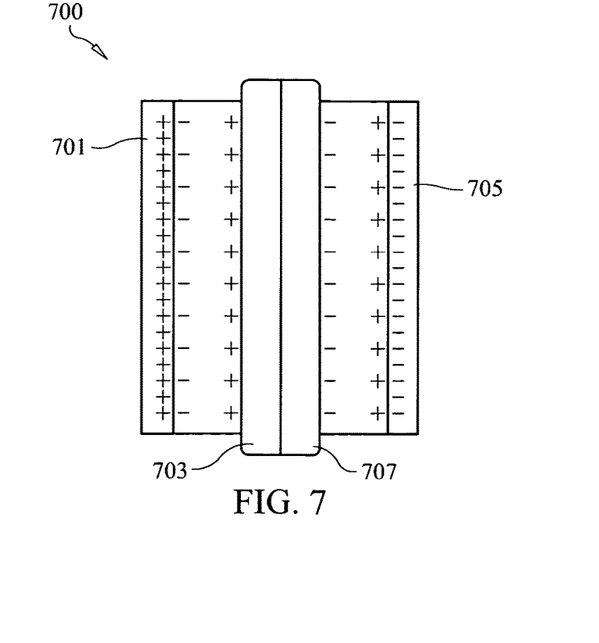
FIG. 7 is a schematic representation of an electrostatic latch in accordance with an illustrative embodiment of the invention.

In this embodiment, the microprocessor controlled array is made up of electroadhesors 164 incorporated into prosthetic socket 105 or liner 103 or into both of them. Liner 103 is preferably composed of elastomeric gel modified to enhance its electroadhesive characteristics. Alternately, liner 103 incorporates an array of small scale and/or flexible electroadhesors 164 which interact directly with electroadhesors 164 in prosthetic socket 105. This configuration, illustrated in FIG. 7, forms electrostatic latch 700 comprising socket side electroadhesor 701, socket side dielectric layer 703, liner side electroadhesor 705 and liner side dielectric 707. Incorporation of electrostatic latch 700 into system 100 maximizes the electrostatic forces providing suspension and limb volume control. While in use, the level of electrostatic adhesion may be adjusted dynamically by microprocessor 143 in response to user demand or sensor data.

In summary, illustrative embodiments of system 100 provide a number of benefits. The electromagnetic force supplied by system 100 can cover the entire residual limb 101 within prosthetic socket 105 without the need for a vacuum seal between residual limb 101 and prosthetic socket 105. This ensures an intimate fit of the prosthesis and serves to limit changes in residual limb volume.

As an electronic device, system 100 may be turned on or off instantly, facilitating donning and doffing of prosthetic socket 105. The strength of the electromagnetic field can be adjusted dynamically, either manually by the user or automatically with the integration of sensors within prosthetic socket 105 and integration of a microprocessor in socket adapter 114 to control the individual electromagnets 107 within array 102. This allows system 100 to dynamically respond to user demands. Array 102 may be configured to allow for customization of the electromagnet distribution and shape of the array, while readily being incorporated into the standard process of prosthetic socket fabrication. There is no requirement for surgical implantation of the any components of system 100. System 100 is an improvement to existing design, allowing for cost effective manufacture and ready integration into prosthetic practice.

Many variations of the invention will occur to those skilled in the art. Some variations include electromagnets. Other variations call for both electromagnets and permanent magnets. All such variations are intended to be within the scope and spirit of the invention.

Although some embodiments are shown to include certain features or steps, the applicants specifically contemplate that any feature or step disclosed herein may be used together or in combination with any other feature or step on any embodiment of the invention. It is also contemplated that any feature or step may be specifically excluded from any embodiment of the invention.

What is claimed is:
1. A suspension system for attaching a prosthetic device to a residual limb, said suspension system comprising:
 a prosthetic socket having a base and sidewalls with an interior surface, said prosthetic socket being is attachable to the prosthetic device;

a non-magnetized liner that is comprised of an outer layer comprising objects of attraction and an inner layer, said liner being operative to be in intimate contact with said residual limb; and a three-dimensional, cup-shaped array comprising a plurality of non-adjacent and spaced apart means for adhering said socket to said non-magnetized liner that are embedded in said sidewalls, but not in said base, of said prosthetic socket, said three-dimensional, cup-shaped array having a circular cross section;

an array hub disposed at said base of said prosthetic socket that is in electrical communication with each of said means for adhering said prosthetic socket to said non-magnetized liner;

a socket adaptor disposed at said base of said prosthetic socket that is in electrical communication with said socket adaptor comprising a microprocessor that is programmed to control the field strength of each of said means for adhering said prosthetic socket to said non-magnetized liner, a power supply for energizing said microprocessor and each of said means for adhering said prosthetic socket to said non-magnetized liner, and a power switch and having a locking pin receptacle; and one or more sensors that are disposed in said prosthetic socket or in said non-magnetized liner or in both of them, each of said one or more sensors being in electrical communication with said microprocessor;

wherein, in use, each of said means for adhering said prosthetic socket to said non-magnetized liner is operative not to cause such adherence between said prosthetic socket and said non-magnetized liner when the suspension system is switched off using said power switch, facilitating a user's insertion of a liner-clad residual limb into said prosthetic socket;

wherein, in use, each of said means for adhering said prosthetic socket to said non-magnetized liner is operative to be attracted to said non-magnetized liner and to prevent axial and rotational movement of said liner-clad residual limb relative to said prosthetic socket when the suspension system is switched on;

wherein the field strength of each of said means for adhering said socket to said non-magnetized liner is controlled by said microcontroller in response to signals from said one or more sensors;

wherein, in use, the suspension system is operative to suspend and control the volume of the residual limb.

2. The suspension system of claim 1 wherein said one or more sensors comprise:

one or more pressure sensors that are disposed in said prosthetic socket or in said non-magnetized liner or in both of them and that are in electrical communication with said microprocessor;

one or more load sensors that are disposed in said prosthetic socket or in said non-magnetized liner or in both of them and that are in electrical communication with said microprocessor; and one or more position sensors that are disposed in said prosthetic socket or in said non-magnetized liner or in both of them and that are in electrical communication with said microprocessor.

3. The suspension system of claim 1 further comprising: active means for generating a suction for attaching said non-magnetized liner to the residual limb.

4. The suspension system of claim 1 further comprising: wired or wireless communication means on said socket adaptor for communication with a computer or handheld device.

5. The suspension system of claim 1 wherein said means for adhering said socket to said non-magnetized liner comprises a plurality of first electromagnets, a plurality of first electropermanent magnets, or a plurality of first electroadhesors, wherein each of said first electromagnets, said first electropermanent magnets, or said first electroadhesors is connected to said array hub by a lead.

6. The suspension system of claim 1 wherein said three-dimensional, cup-shaped array comprises a plurality of electromagnets, a plurality of electropermanent magnets, or a plurality of electroadhesors that are arranged in a spider web fashion to facilitate fitting said three-dimensional, cup-shaped array into said prosthetic socket.

7. The suspension system of claim 1 wherein said three-dimensional, cup-shaped array is flexible to allow it to conform to the shape of said prosthetic socket.

8. The suspension system of claim 1 wherein said inner layer is composed of a silicone gel.

9. The suspension system of claim 1 wherein said outer layer comprises a non-magnetized magnetically active material.

10. The suspension system of claim 9 wherein said non-magnetized magnetically active material is bonded to said inner layer.

11. The suspension system of claim 1 wherein said socket adaptor further comprises:

a wired communication device or a wireless communication device to allow for adjustments to said three-dimensional cup-shaped array to be made using a computer or a handheld device.

12. A suspension system for attaching a prosthetic device to a residual limb, said suspension system comprising:

a prosthetic socket having sidewalls with an interior surface, said prosthetic socket being attachable to the prosthetic device;

a plurality of electromagnets that are non-adjacent and spaced apart, arranged in a spider web fashion in a three-dimensional, cup-shaped array, and embedded in the sidewalls, but not the base, of said prosthetic socket;

a socket adaptor that is incorporated into the base of said prosthetic socket, said socket adaptor being in electrical communication with each of said electromagnets and comprising a microprocessor that is programmed to control the field strength of each of said electromagnets, a power supply for energizing said microprocessor and said electromagnets, and a power switch and having a locking pin receptacle;

a magnetically active liner that is comprised of an outer layer that is fabricated from a non-magnetized magnetically active material and an inner layer that is composed of an elastomeric gel, said magnetically active liner being operative to be in intimate contact with said residual limb;

one or more sensors that are disposed in said socket or in said magnetically active liner or in both of them, each of said one or more sensors being in electrical communication with said microcontroller; and a locking pin that protrudes from said magnetically active liner and that is adapted to fit into said locking pin receptacle and to attach the prosthetic device to the residual limb;

wherein, in use, each of said electromagnets is operative not to produce a magnetic field when the suspension system is switched off using said power switch, facilitating a user's insertion of a liner-clad residual limb into said prosthetic socket;

wherein, in use, each of said first electromagnets is operative to be attracted to said liner and to prevent axial and rotational movement of said liner-clad residual limb relative to said prosthetic socket when the suspension system is switched on;

wherein, in use, the strength of each of said magnetic fields is controlled by said microprocessor in response to electrical signals from said one or more sensors;

wherein, in use, the system is operative to suspend and control the volume of the residual limb.

13. The suspension system of claim 12 wherein said electromagnets are attached to a support lattice.

14. The suspension system of claim 12 wherein said one or more sensors comprise:

one or more pressure sensors that are disposed in said prosthetic socket or in said magnetically active liner or in both of them and that are in electrical communication with said microprocessor;

one or more load sensors that are disposed in said prosthetic socket or in said magnetically active liner or in both of them and that are in electrical communication with said microprocessor; and one or more position sensors that are disposed in said prosthetic socket or in said magnetically active liner or in both of them and that are in electrical communication with said microprocessor.

15. The suspension system of claim 12 further comprising:

active means for generating a suction for attaching said non-magnetized magnetically active liner to the residual limb.

16. The suspension system of claim 12 wherein said socket adapter further comprises:

wireless communication means for communication with a computer or handheld device.

* * * * *